United States Patent
Westenbrink

(10) Patent No.: US 11,365,728 B2
(45) Date of Patent: Jun. 21, 2022

(54) TESTING ROTOR ENGAGEMENT OF A ROTARY PERISTALTIC PUMP

(71) Applicant: Quanta Dialysis Technologies Ltd., Warwickshire (GB)

(72) Inventor: Eric Westenbrink, Warwickshire (GB)

(73) Assignee: Quanta Dialysis Technologies Ltd., Warwickshire (GB)

( * ) Notice: Subject to any disclaimer, the term of this patent is extended or adjusted under 35 U.S.C. 154(b) by 272 days.

(21) Appl. No.: 16/488,499

(22) PCT Filed: Feb. 23, 2018

(86) PCT No.: PCT/GB2018/050477
§ 371 (c)(1),
(2) Date: Aug. 23, 2019

(87) PCT Pub. No.: WO2018/154317
PCT Pub. Date: Aug. 30, 2018

(65) Prior Publication Data
US 2019/0376504 A1    Dec. 12, 2019

(30) Foreign Application Priority Data
Feb. 24, 2017    (GB) .................................... 1703048

(51) Int. Cl.
*F04B 43/12*        (2006.01)
*F04B 43/00*        (2006.01)
(Continued)

(52) U.S. Cl.
CPC ...... *F04B 43/1253* (2013.01); *F04B 43/0072* (2013.01); *F04B 43/0081* (2013.01);
(Continued)

(58) Field of Classification Search
CPC .. F04B 43/0081; F04B 43/1253; F04B 43/12; A61M 5/14232; A61M 60/279
See application file for complete search history.

(56) References Cited

U.S. PATENT DOCUMENTS 3,774,762 A    11/1973    Lichtenstein
4,161,264 A    7/1979    Malmgren
(Continued)

FOREIGN PATENT DOCUMENTS

DE    10024447 A1    11/2001
EP    0165751 A2    12/1985
(Continued)

OTHER PUBLICATIONS

Search Report for application GB1703048.7, dated Aug. 24, 2017.
Search Report and Written Opinion for International Applicaiton No. PCT/GB2018/050477, dated Apr. 26, 2018.

*Primary Examiner* — Christopher S Bobish
(74) *Attorney, Agent, or Firm* — Cooley LLP

(57) ABSTRACT

A method of testing the rotor engagement of a peristaltic pump rotor. The method comprising steps of providing a pump system comprising a peristaltic pump rotor; a tube; a valve; a pressure sensor; a comparator; and a processor. The pressure sensor is configured to monitor the pressure in a fluid in the tube downstream of the peristaltic pump rotor and upstream of the valve. The comparator is configured to continuously monitor the pressure sensor and compare the measured fluid pressure data with a predetermined parameter. The processor is configured to receive a signal from the comparator and generate an alert signal when the measured pressure data falls outside the predetermined parameters.

20 Claims, 10 Drawing Sheets

(51) Int. Cl.
    *A61M 5/142*         (2006.01)
    *A61M 60/279*      (2021.01)

(52) U.S. Cl.
    CPC ......... *F04B 43/12* (2013.01); *A61M 5/14232* (2013.01); *A61M 60/279* (2021.01)

(56) References Cited

U.S. PATENT DOCUMENTS

| | | | |
|---|---|---|---|
| 4,353,990 | A | 10/1982 | Manske et al. |
| 4,366,061 | A | 12/1982 | Papanek et al. |
| 4,599,165 | A | 7/1986 | Chevallet |
| D308,249 | S | 5/1990 | Buckley |
| 4,969,991 | A | 11/1990 | Valadez |
| 5,000,664 | A | 3/1991 | Lawless et al. |
| 5,032,265 | A | 7/1991 | Jha et al. |
| 5,055,198 | A | 10/1991 | Shettigar |
| 5,103,211 | A | 4/1992 | Daoud et al. |
| 5,252,213 | A | 10/1993 | Ahmad et al. |
| D341,890 | S | 11/1993 | Sievert et al. |
| D344,339 | S | 2/1994 | Yoshikawa et al. |
| D351,470 | S | 10/1994 | Scherer et al. |
| 5,421,823 | A | 6/1995 | Kamen et al. |
| 5,476,792 | A | 12/1995 | Ezrielev et al. |
| D370,979 | S | 6/1996 | Pascale et al. |
| 5,591,344 | A | 1/1997 | Kenley et al. |
| 5,643,201 | A | 7/1997 | Peabody et al. |
| 5,658,456 | A | 8/1997 | Kenley et al. |
| 5,665,307 | A | 9/1997 | Kirschner et al. |
| 5,807,322 | A * | 9/1998 | Lindsey ............ A61M 5/16859 604/65 |
| 5,948,247 | A | 9/1999 | Gillerfalk et al. |
| 6,126,831 | A | 10/2000 | Goldau et al. |
| 6,153,102 | A | 11/2000 | Kenley et al. |
| 6,251,279 | B1 | 6/2001 | Peterson et al. |
| 6,514,462 | B1 | 2/2003 | Simons |
| 6,558,347 | B1 * | 5/2003 | Jhuboo ............ A61M 5/14228 604/151 |
| 6,663,829 | B1 | 12/2003 | Kjelistrand |
| 6,967,002 | B1 | 11/2005 | Edgson et al. |
| 7,107,837 | B2 | 9/2006 | Lauman et al. |
| 7,284,964 | B2 * | 10/2007 | McDowell ............ F04B 43/009 417/477.1 |
| 7,648,627 | B2 | 1/2010 | Beden et al. |
| 7,896,197 | B2 * | 3/2011 | Furey ................. F04B 43/1253 222/64 |
| D641,882 | S | 7/2011 | Hickey et al. |
| 8,535,525 | B2 | 9/2013 | Heyes et al. |
| D693,469 | S | 11/2013 | Chung et al. |
| 8,685,244 | B2 | 4/2014 | Heyes et al. |
| D724,740 | S | 3/2015 | Collins et al. |
| 9,220,825 | B2 | 12/2015 | Buckberry |
| 9,744,285 | B2 | 8/2017 | Heyes et al. |
| 9,833,553 | B2 | 12/2017 | Higgitt et al. |
| 10,456,516 | B2 | 10/2019 | Heyes et al. |
| 10,543,305 | B2 | 1/2020 | Buckberry et al. |
| D907,211 | S | 1/2021 | Spurling |
| 10,881,775 | B2 | 1/2021 | Wallace |
| 10,960,120 | B2 | 3/2021 | Wallace et al. |
| 2003/0217962 | A1 | 11/2003 | Childers et al. |
| 2004/0195157 | A1 | 10/2004 | Mullins et al. |
| 2004/0206703 | A1 | 10/2004 | Bosetto et al. |
| 2004/0215129 | A1 | 10/2004 | Edgson et al. |
| 2004/0223857 | A1 | 11/2004 | Kline |
| 2005/0020961 | A1 | 1/2005 | Burbank et al. |
| 2005/0205476 | A1 | 9/2005 | Chevallet et al. |
| 2005/0209547 | A1 | 9/2005 | Burbank et al. |
| 2005/0234384 | A1 | 10/2005 | Westberg |
| 2006/0121623 | A1 | 6/2006 | He et al. |
| 2007/0083193 | A1 | 4/2007 | Werneth et al. |
| 2008/0283096 | A1 | 11/2008 | Scheringer et al. |
| 2009/0007642 | A1 | 1/2009 | Busby et al. |
| 2009/0009290 | A1 | 1/2009 | Kneip et al. |
| 2009/0012450 | A1 | 1/2009 | Shan et al. |
| 2009/0012452 | A1 | 1/2009 | Slepicka et al. |
| 2009/0012457 | A1 | 1/2009 | Childers et al. |
| 2009/0101550 | A1 | 4/2009 | Muller et al. |
| 2009/0211975 | A1 | 8/2009 | Brugger et al. |
| 2009/0230043 | A1 | 9/2009 | Heyes et al. |
| 2010/0043694 | A1 | 2/2010 | Patel |
| 2010/0045471 | A1 | 2/2010 | Meyers |
| 2010/0089807 | A1 | 4/2010 | Heyes et al. |
| 2010/0139254 | A1 | 6/2010 | Sebestyen et al. |
| 2010/0263687 | A1 | 10/2010 | Braun et al. |
| 2011/0009797 | A1 | 1/2011 | Kelly et al. |
| 2011/0034850 | A1 | 2/2011 | Jonsson |
| 2011/0132838 | A1 | 6/2011 | Curtis et al. |
| 2011/0168614 | A1 | 7/2011 | Pouchoulin et al. |
| 2012/0164022 | A1 | 6/2012 | Muginstein et al. |
| 2012/0292237 | A1 | 11/2012 | Heyes et al. |
| 2012/0308431 | A1 | 12/2012 | Kotsos et al. |
| 2013/0056419 | A1 | 3/2013 | Curtis |
| 2013/0153495 | A1 | 6/2013 | Kelly et al. |
| 2013/0199998 | A1 | 8/2013 | Kelly et al. |
| 2013/0274642 | A1 | 10/2013 | Soykan et al. |
| 2014/0224736 | A1 | 8/2014 | Heide |
| 2014/0251885 | A1 | 9/2014 | Heyes |
| 2014/0299544 | A1 | 10/2014 | Wilt et al. |
| 2015/0027951 | A1 | 1/2015 | Wallace et al. |
| 2015/0076053 | A1 | 3/2015 | Higgitt et al. |
| 2015/0112119 | A1 | 4/2015 | Buckberry |
| 2015/0129481 | A1 | 5/2015 | Higgitt et al. |
| 2015/0238673 | A1 | 8/2015 | Gerber et al. |
| 2015/0258263 | A1 | 9/2015 | Hogard |
| 2015/0359954 | A1 | 12/2015 | Gerber et al. |
| 2016/0045656 | A1 | 2/2016 | Buckberry |
| 2016/0051743 | A1 | 2/2016 | Buckberry |
| 2016/0058933 | A1 | 3/2016 | Ballantyne et al. |
| 2017/0252498 | A1 | 9/2017 | Heyes et al. |
| 2018/0133391 | A1 | 5/2018 | Heyes et al. |
| 2018/0154059 | A1 | 6/2018 | Heyes et al. |
| 2018/0344915 | A1 | 12/2018 | Wallace |
| 2019/0001042 | A1 | 1/2019 | Buckberry |
| 2019/0015577 | A1 | 1/2019 | Garrido et al. |
| 2019/0024654 | A1 | 1/2019 | May et al. |
| 2019/0358381 | A1 | 11/2019 | Westenbrink |
| 2019/0374698 | A1 | 12/2019 | Buckberry et al. |
| 2020/0030515 | A1 | 1/2020 | Merchant |
| 2020/0268958 | A1 | 8/2020 | Heyes et al. |
| 2020/0276372 | A1 | 9/2020 | Milad et al. |
| 2020/0330671 | A1 | 10/2020 | Buckberry et al. |
| 2022/0001087 | A1 | 1/2022 | Heyes et al. |

FOREIGN PATENT DOCUMENTS

| | | |
|---|---|---|
| EP | 2219703 A1 | 8/2010 |
| EP | 2955512 A1 | 12/2015 |
| JP | H04266740 | 9/1992 |
| JP | H06261872 | 9/1994 |
| JP | H07174659 | 7/1995 |
| JP | 2000/130334 | 5/2000 |
| WO | WO 81/01800 | 7/1981 |
| WO | WO 95/06205 | 3/1995 |
| WO | 95025893 A2 | 9/1995 |
| WO | WO 2000/006217 | 2/2000 |
| WO | WO 2003/101510 | 12/2003 |
| WO | WO 2006/120415 | 11/2006 |
| WO | WO 2006/120417 | 11/2006 |
| WO | WO 2009/061608 | 5/2009 |
| WO | 2013057109 A1 | 4/2013 |
| WO | WO 2013/110906 | 8/2013 |
| WO | WO 2013/110919 | 8/2013 |
| WO | WO 2013/114063 | 8/2013 |
| WO | WO 2013/121162 | 8/2013 |
| WO | WO 2013/121163 | 8/2013 |
| WO | 2014072195 A1 | 5/2014 |
| WO | WO 2014/155121 | 10/2014 |
| WO | WO 2015/007596 | 1/2015 |
| WO | WO 2015/022537 | 2/2015 |
| WO | WO 2016/016870 | 2/2016 |
| WO | WO 2017/137723 | 8/2017 |
| WO | WO 2018/115816 | 6/2018 |

* cited by examiner

TESTING ROTOR ENGAGEMENT OF A ROTARY PERISTALTIC PUMP

RELATED APPLICATIONS

This application is a 371 National Stage Filing of PCT application no. PCT/GB2018/050477, having an international filing date of Feb. 23, 2018, which claims priority to GB1703048.7, having a filing date of Feb. 24, 2017. Each of the foregoing disclosures, in its entirety, is incorporated herein by reference.

TECHNICAL FIELD

The present invention relates to a method of testing the rotor engagement of a rotary peristaltic pump, and particularly but not exclusively to a rotary peristaltic pump used in dialysis machinery.

BACKGROUND TO THE INVENTION

Rotary peristaltic pumps are a common type of positive displacement pump used for pumping a variety of fluids. The fluid is pumped by subjecting a flexible tube arranged in a race to a series of successive compressions which act to drive the fluid along the tube.

A common mechanism to provide this successive compression force is to arrange tubing in a race formed by a hollow chamber having a U-shaped end, and to trap the tubing between a rotor having a plurality of protrusions and the wall of the pump race. As such, when the rotor is turned, the protrusions of the rotor compress a portion of tubing and move along the tubing squeezing the contained fluid along.

Typically, there are two or three protrusions attached to the rotor, and on the end of each protrusion there is generally a wheel or roller which engages with the flexible tubing.

Typically, the protrusion is moveable relative to the rotor and is biased away from the drive axis of rotation of the rotor by a spring.

For the rotary peristaltic pump to pump correctly, the flexible tubing must be squeezed or occluded sufficiently to prevent the escape or backflow of the fluid contained within the flexible tube.

This is particularly important when the rotary peristaltic pump is being used in a dialysis machine. This is because proper functioning of the dialysis machine relies on sufficient downstream pressure. Should the rollers on the end of the protrusions not sufficiently occlude the flexible tube there will be a lack of pressure generated downstream of the rotary peristaltic pump, potentially inhibiting proper functioning of the dialysis machine.

In addition, with the rollers correctly occluding the flexible tubing, the effect of a failure elsewhere in a dialysis machine can be mitigated since the occlusion of the flexible tubing interrupts the free flow of fluid therethrough.

An inability of the rollers effectively to occlude the flexible tube may be caused by a number of factors. In one instance, a deformity in the outer race against which the flexible tubing is pressed by the roller to create an occlusion may prevent complete occlusion. In another instance, the biasing spring which acts upon the roller to create an occluding force may fatigue and the spring rate decrease thereby reducing the effectiveness of the spring in creating an occlusion. In yet another instance the flexible tubing may split and leak.

Furthermore, the flexible tubing may become less compliant due to environmental factors such as low temperatures, thereby inhibiting the roller from correctly occluding the flexible tubing due to increased stiffness of the tube. The flexible tubing may also become less compliant due to the flexible tubing becoming fatigued.

The object of the present invention is to provide an improved method of testing the engagement of a rotary peristaltic pump.

SUMMARY OF THE INVENTION

A method for testing the rotor engagement and resulting occlusion of a flexible tube in a rotary peristaltic pump is provided to ensure correct occlusion of a flexible tube and correct operation of the peristaltic pump.

According to the present invention, there is provided a method of testing the rotor engagement of a peristaltic pump, the method comprising the steps of:

a) providing a pump system comprising a peristaltic pump rotor, a tube, a valve, a pressure sensor, a comparator, and a processor, wherein the valve is situated on the tube downstream of the peristaltic pump rotor, the pressure sensor is arranged to sense the fluid pressure in the tube at a position downstream of the peristaltic pump rotor and upstream of the valve, the peristaltic pump rotor including at least one member having a tube contact portion, the at least one member being rotatable about a drive axis to move the tube contact portion along an arcuate path, the tube contact portion being configured to occlude the tube;
b) providing a fluid in the tube;
c) arranging the pump system such that the valve is open, the peristaltic pump rotor is inactive and the tube contact portion is occluding the tube;
d) closing the valve;
e) actuating the peristaltic pump rotor from a first rotor position to a second rotor position such that the peristaltic pump rotor is angularly displaced about the drive axis by a predetermined priming angular displacement;
f) holding the peristaltic pump rotor in the second rotor position for a holding interval of predetermined duration;
g) using the pressure sensor to measure maximum pressure of the fluid in the tube downstream of the peristaltic pump rotor during and/or after completing step e);
h) using the pressure sensor to measure any pressure drop in the fluid in the tube downstream of the peristaltic pump rotor during the holding interval;
i) using the processor to generate an alert signal if the maximum pressure recorded in step g) is below a first predetermined threshold value and/or the pressure drop measured in step h) is above a second predetermined threshold value;

The method may further comprise step j), wherein step j) comprises opening the valve and using the pressure sensor to determine when the fluid pressure in the tube is lower than a third predetermined threshold.

The collated and or recorded data may be used for interrogating the function of the rotary peristaltic pump.

Steps d) to j) may repeated a primary predetermined number of times to test the peristaltic pump rotor in a number positions thereby improving the accuracy of the test. Preferably the primary predetermined number of times is two.

The method may further comprise step k), wherein step k) comprises actuating the peristaltic pump rotor such that the peristaltic pump rotor may be angularly displaced about the drive axis by a predetermined switchover angle. The predetermined switchover angle may be in the range of 10 to 170 degrees. Preferably, the predetermined switchover angle is 60 degrees. Providing a switchover angle of 60 degrees increases efficiency by optimising the method so that each of the members is tested three times at different angular positions relative to the drive axis when two members are provided. Angularly displacing the peristaltic pump rotor by a switchover angle facilitates the testing of the tube with the peristaltic pump rotor in different positions. By adjusting the magnitude of the predetermined switchover angle, each roller of the pump rotor may be tested in different positions relative to the drive axis to test that the members and related tube contact portion are occluding the tube correctly and that there are no leaks.

Pressure drop may be defined in terms of an absolute value or in terms of rate of change of the pressure. That is the absolute value of the change in pressure divided by the time over which that change took place. The second predetermined threshold value may be an absolute e.g. 100 mmHg or a rate of change e.g. 10 mm Hgmms$^{-1}$ depending on how the pressure drop is measured.

Following the completion of step k), steps d) to j) may be repeated a secondary predetermined number of times. The secondary predetermined number of times is preferably three.

The predetermined holding interval may be in the range of 5 to 60 seconds. Preferably, the predetermined holding interval is 10 seconds.

The first predetermined threshold value may be in the range of 75 mmHg (9999.18 Pa) to 1500 mmHg (199983.59 Pa). Preferably, the first predetermined threshold value is 200 mmHg (2664.48 Pa).

The second predetermined threshold value may be in the range of 50 mmHg (6666.12 Pa) to 1475 mmHg (196650.53) or alternatively in the range of 0.83 mmHgs$^{-1}$ (111.10 Pas$^{-1}$) to 295 mmHgs$^{-1}$ (39330.11 Pas$^{-1}$). Preferably, the second predetermined threshold value is 175 mmHg (23331.42 Pa), alternatively the second predetermined threshold value is 17.5 mmHgs$^{-1}$ (2333.14 Pas$^{-1}$).

The third predetermined threshold value may be in the range of 0 mmHg (0 Pa) to 1450 mmHg (193317.47 Pa). Preferably, the third predetermined threshold value is 75 mmHg (9999.18 Pa).

The predetermined priming angular displacement may be in the range of 10 to 350 degrees. Preferably, the predetermined priming angular displacement is 240 degrees.

The processor may be used to generate a pass signal if no alert signals are generated.

The alert signal may be used to generate an alarm signal. The alarm signal may be generated by a signal generator and the generated alarm signal may be audio and/or visual.

The method may be terminated when an alert signal is generated.

The fluid being pumped may be blood or the fluid being pumped may be saline solution or another type of fluid used in blood dialysis.

The tube may be held within a U-Shaped channel in an outer race of a housing.

The pump system may automatically run the method when the pump system is activated.

The valve may be a pinch clamp which may be configured to occlude the tube.

The tube contact portion may comprise a roller.

There may be two members provided and the two members may be diametrically opposed.

There may be three members provided and the three members may be equally spaced angularly about the drive axis.

The invention will now be described with reference to the accompanying drawings.

SPECIFIC DESCRIPTION

Figure 1:
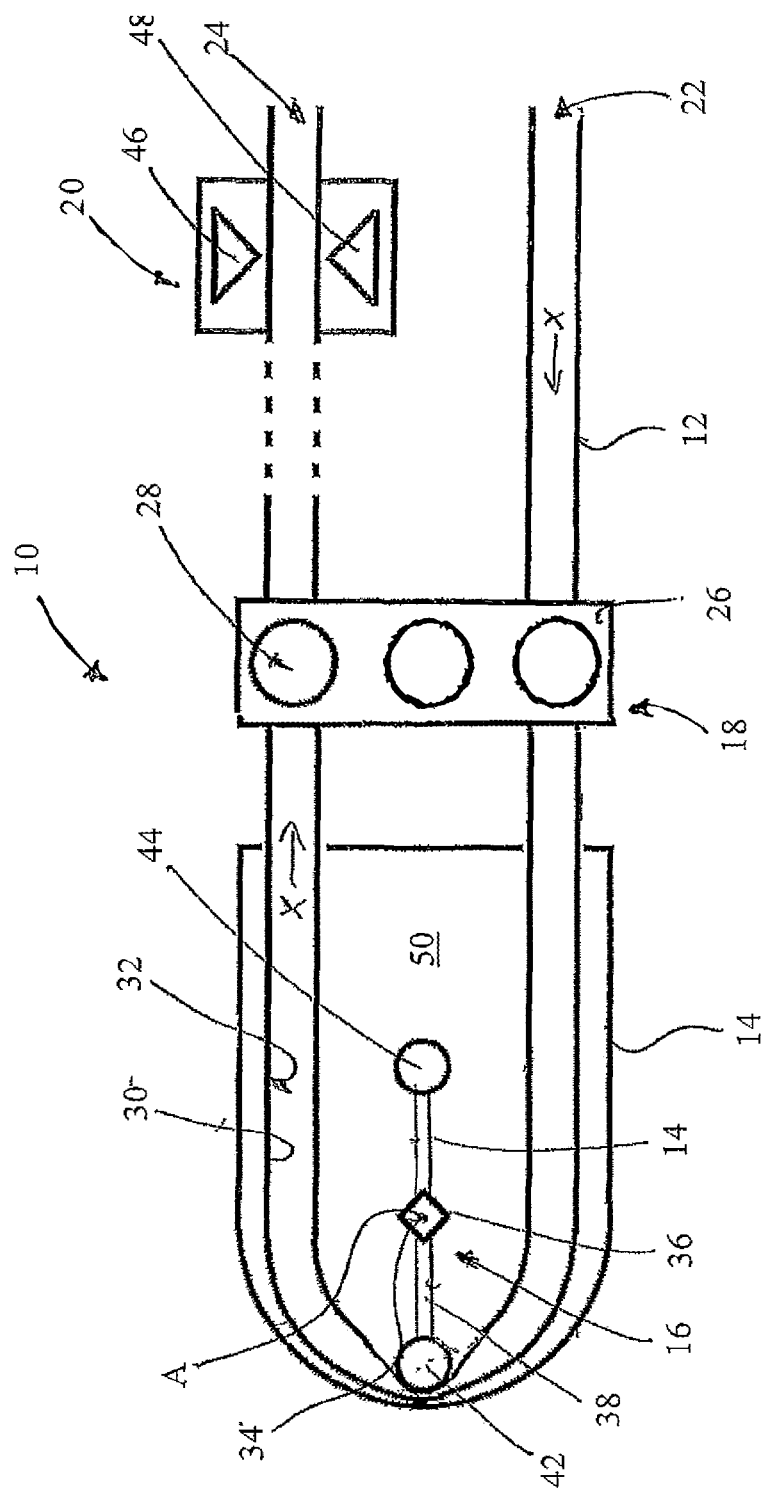
FIG. 1 is a schematic side view of a rotary peristaltic pump with the rollers in an initial position, operating the method of the present invention.

In FIGS. 1 to 8, the rotary peristaltic pump 10 is pictured schematically at various positions during a test cycle which incorporates the method of the present invention.

The rotary peristaltic pump 10 comprises a tube 12, a pump housing 14, a peristaltic pump rotor 16, a sensor module 18 and a valve 20.

The tube 12 is elongate and has an inlet 22 at its upstream end and an outlet 24 at its downstream end. The tube 12 is made from a flexible material such as medical grade polyvinylchloride.

The pump housing 14 comprises a structure with a U-shaped wall 30 defining a U-shaped space 32 and a drive shaft 34. The pump housing 14 is manufactured using high pressure injection moulding of plastic. The drive shaft 34 protrudes through a back wall 50 of the pump housing 14 and is configured to be driven by a motor (not shown). The drive shaft 34 defines a drive axis A.

The peristaltic pump rotor 16, in this simplified embodiment comprises a hub 36 and two, diametrically opposed arms 38, 40 arranged on either side of the hub 36 and projecting therefrom. Each arm has a tube contact portion in the form of a roller 42, 44 arranged respectively at the projecting end thereof.

The sensor module 18 comprises a sensor housing 26 and a pressure sensor 28. The sensor housing 26 is made from injection moulded plastic. The pressure sensor 28 is an electromagnetic pressure sensor 28, for example as described in WO2011027117A3.

The valve 20 is a pinch clamp type valve and has bicuspid structures 46, 48 that are moveable between an open and a closed position.

The tube 12 extends from the inlet 22 into the sensor housing 26 of the sensor module 18, passing next into the pump housing 14 and is arranged to follow the U-shaped wall 30 before emerging from the pump housing 14 to extend through sensor housing 26 of the sensor module 18 and to the outlet 24.

The peristaltic pump rotor 16 is arranged within the pump housing 14 on the drive shaft 34 which is arranged at a position in the housing such that, with the hub 36 affixed to the drive shaft 34 and the tube 12 following the U-shaped wall 30, the rollers 42, 44 on the arms 38, 40 occlude the tube 12 completely by compressing the tube 12 between the respective roller 42 or 44 and the U-shaped wall 30.

The pressure sensor 28 is positioned in the sensor housing 26 on a portion of the tube 12 that is downstream of the pump housing 14.

The valve 20 is arranged on the tube 12 downstream of the pump housing 14 and the sensor module 18. The valve 20 has two states: open or closed. When the valve 20 is open, the valve 20 does not occlude the tube 12. When the valve 20 is closed, the valve 20 occludes the tube 12.

In operation, the rotary peristaltic pump 10 works as follows.

Fluid enters the tube 12 at the inlet 22, for example by connection of the inlet 22 to an artery and flows in the direction indicated by the arrow X. The fluid flows along the tube 12 and into the part of the tube 12 which enters the pump housing 14. The fluid follows the U-shaped wall 30 of the pump housing 14 before exiting the pump housing 14. The fluid continues along the tube 12 entering into the sensor housing 26 and passing the pressure sensor 28. The fluid next passes through the valve 20.

The fluid is drawn into the tube 12 due to the rotation of the peristaltic pump rotor 16 and the sequential occlusion of the tube 12 by the rollers 42, 44 at the ends of the diametrically opposed arms 38, 40.

In more detail, the motor (not shown), is configured to drive the hub 36 such that the hub 36 rotates clockwise about the drive axis A. As the arms 38, 40 are rigidly attached to the hub 36, the arms 38, 40 are also rotated about the drive axis A. The rollers 42, 44 positioned at the end of each arm are thus moved along an arcuate path. As the rollers 42, 44 are rotated about the drive axis A, they act on the tube 12 to sequentially occlude the tube 12 alternately with each half rotation of the hub 36. The sequential occlusion of the tube 12 by the rollers 42, 44 draws fluid from the inlet 22 of the tube 12 upstream of the pump housing 14 and pushes the fluid out of the pump housing 14 towards the outlet 24 of the tube 12.

When the valve 20 is open, the pressure of the fluid in the tube 12 upstream and downstream of the pump housing 14 will be substantially the same. However, when the valve 20 is closed and the peristaltic pump rotor 16 is actuated, i.e. driven to rotate by the motor, the fluid downstream of the pump housing 14 has nowhere to flow to. As such, the pressure of the fluid upstream of the valve 20 and downstream of the pump housing 14 increases.

As the pressure sensor 28 is arranged on the tube 12 between the valve 20 and the pump housing 14, the pressure rise caused by the pumping action of the peristaltic pump rotor 16 and the occlusion of the tube 12 by the valve 20, can be measured.

As will be appreciated the rotary peristaltic pump 10 of the present invention can form part of a larger system such as a pump system 11 of a dialysis machine 50.

Figure 9:
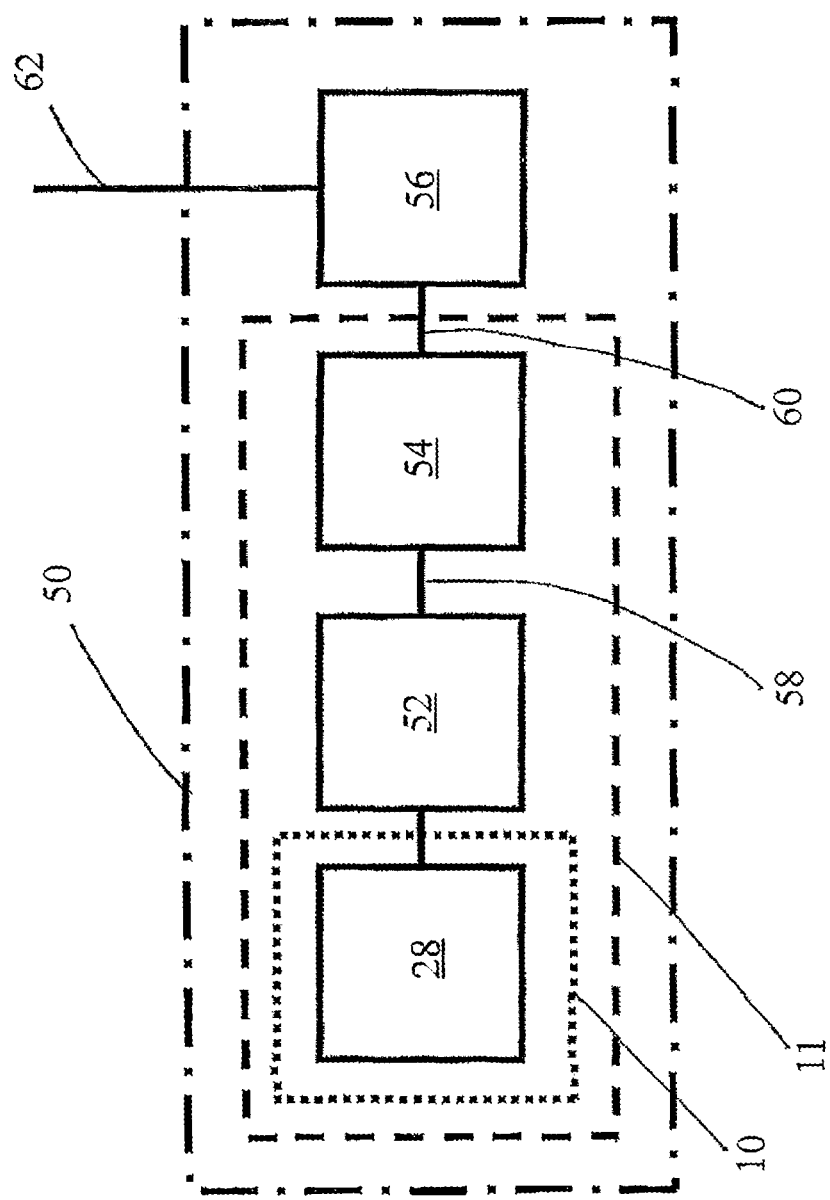
FIG. 9 is a schematic view of a dialysis machine including the rotary peristaltic pump of FIG. 1.
Figure 10:
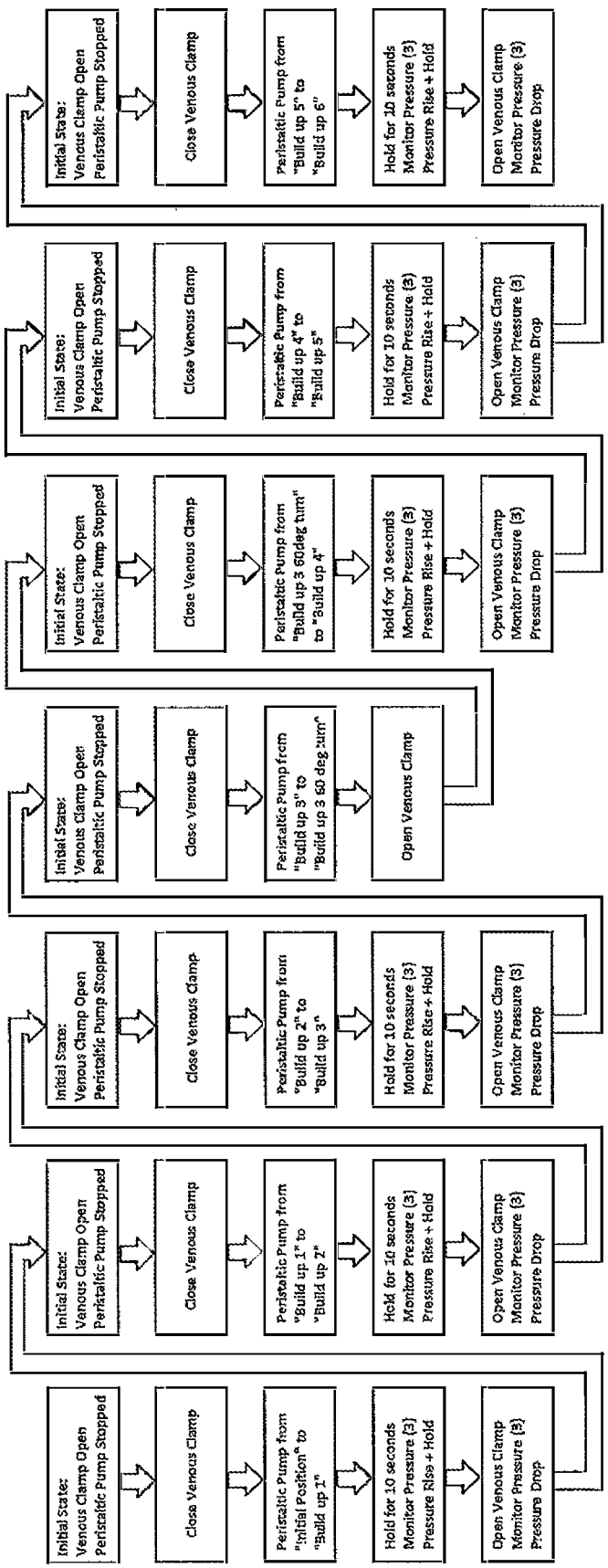
FIG. 10 is a flow chart of the steps of the test procedure embodying the method of the present invention.

In FIG. 9, the dialysis machine 50 is pictured schematically.

The dialysis machine 50 includes a pump system 11 and a processor 54. The pump system 11 includes the rotary peristaltic pump 10, a comparator 52, and a processor 54. The rotary peristaltic pump 10 includes the pressure sensor 28.

The comparator is configured to monitor the pressure data measured by the pressure sensor 28 and to provide an output signal 58 accordingly, and the processor 54 is arranged to receive the output signal 58.

The processor 54 is configured to interpret the output signal 58 and provide an alert signal 60 to the signal generator 56, accordingly, the signal generator 56 is configured to generate audible/visible warnings or alarms 62 when the recorded pressure data falls outside the predetermined parameters.

The alert signal 60 can also be an "everything is functioning correctly" or a "pass" signal, following the data capture of a pressure reading.

The method of the present invention operates as follows:

Referring to FIG. 1, the peristaltic pump rotor 16 is shown in an initial position. When in the initial position the rollers 42, 44 can be in any stationary position about the drive axis A. In this case, the roller 42 is occluding the tube 12 and the valve 20 is open. At this point the test cycle which operates the method of the present invention is ready to begin.

The valve 20 is actuated such that its state is changed from open to closed, this is the initial closing of the valve 20 (step d) in the claimed method).

Figure 2:
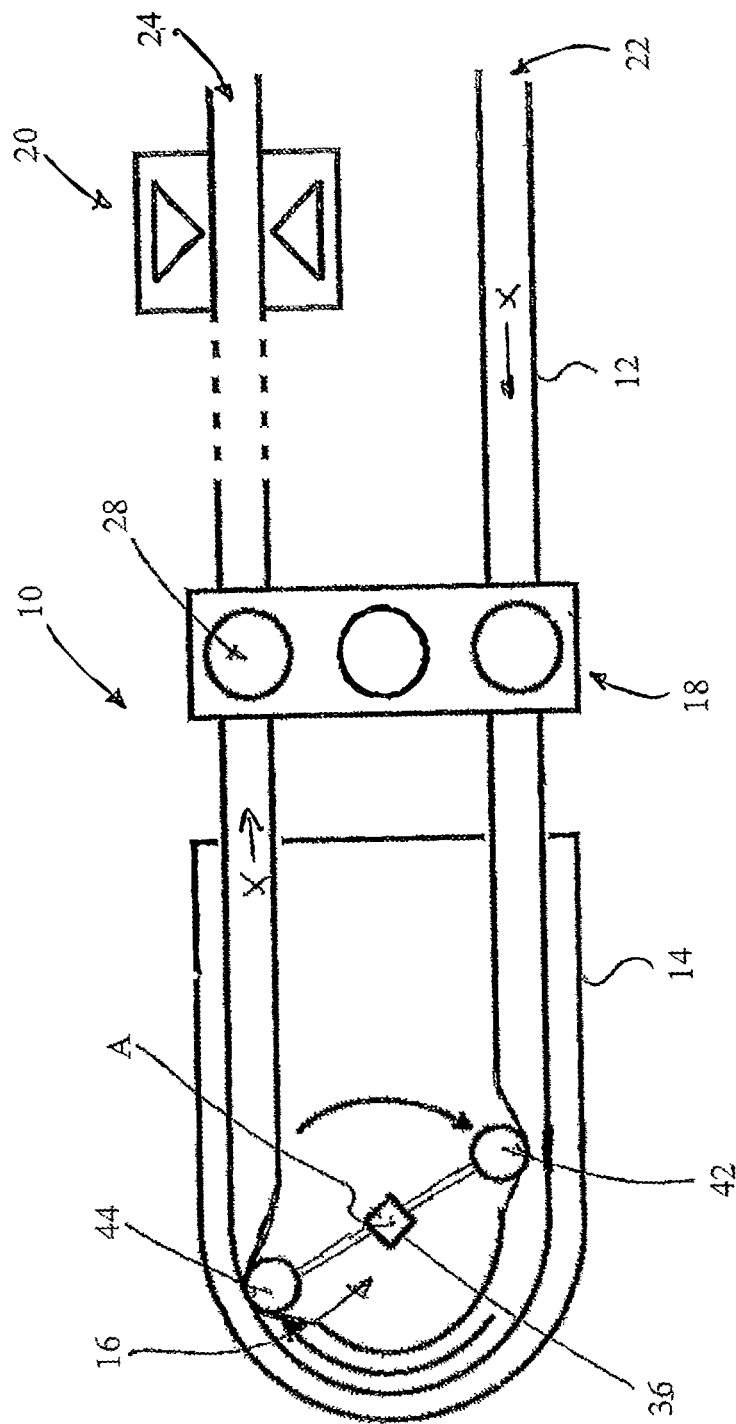
FIG. 2 is a schematic side view of the rotary peristaltic pump of FIG. 1 with the rollers in a first build up position.

The motor is operated to rotate the peristaltic pump rotor 16, that is, the hub 36, the arms 38, 40 and, the rollers 42, 44 about the drive axis A, thereby moving the rollers 42, 44 from the initial position shown in FIG. 1, along an arcuate path to another stationary position as is shown in FIG. 2. The position of the peristaltic pump rotor 16 is displaced from the initial position by a predetermined priming angular displacement, in this example, 240 degrees clockwise. Roller 44 is thus rotated from a "3 o'clock" position in FIG. 1 to an "11 o'clock" position in FIG. 2. The motor drives the peristaltic pump rotor 16 to rotate at a speed which, if valve 20 were in an open state, would produce a flow rate of 50 mL/min at the outlet 24 of the tube 12. However, valve 20 is closed when the rollers 42, 44 are rotated, and as such the pressure of the fluid in the tube 12 downstream of the roller 44 that is presently occluding the tube 12 is increased.

The maximum pressure of the fluid in the tube 12 downstream of the occlusion caused by the roller 44 of the peristaltic pump rotor 16 and upstream of the valve 20 is measured by the pressure sensor 28 and recorded by a CPU 54 or processor.

The rollers 42, 44 are held by the motor in stasis in the position shown in FIG. 2 with the roller 44 occluding the tube 12, for a holding interval of predetermined duration, in this example 10 seconds.

The pressure sensor 28 is configured to continually measure the pressure in the tube 12 downstream of the peristaltic pump rotor 16 and upstream of the valve 20 during the holding interval. The pressure readings are collected by the comparator 52. From the pressure sensor data recorded the maximum pressure of the fluid following the rotation of the peristaltic pump rotor 16 and any pressure drop in the fluid in the tube 12 during the holding interval can be calculated.

In the scenario where no alert signals are generated by the signal generator the method will continue uninterrupted.

The rotary pump is held in stasis and the valve 20 is opened to release the pressure generated in the fluid in the tube 12 during actuation of the peristaltic pump rotor 16. The method will not proceed until the pressure in the fluid in the tube 12 is less than the third predetermined threshold value of approximately 75 mmHg.

To test the correct occlusion of the tube 12 by the rollers 42, 44 in more depth the method can be repeated as follows:

Following the opening of the valve 20 and after the third predetermined threshold value has been passed, the valve 20 is once again closed (step d) of the claimed method) and the scenario described above, following the initial closing of the valve 20 is repeated twice more.

Figure 3:
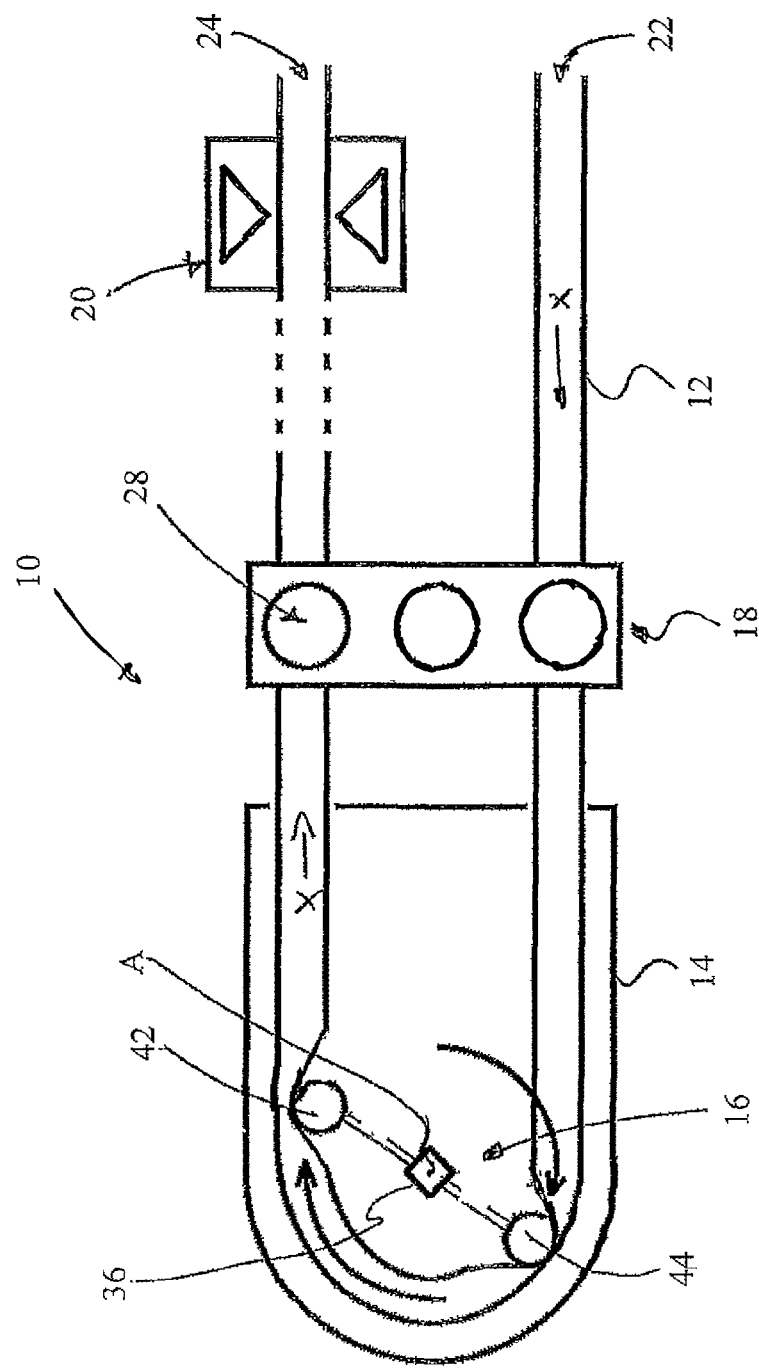
FIG. 3 is a schematic side view of the rotary peristaltic pump of FIG. 1 with the rollers in a second build up position.
Figure 4:
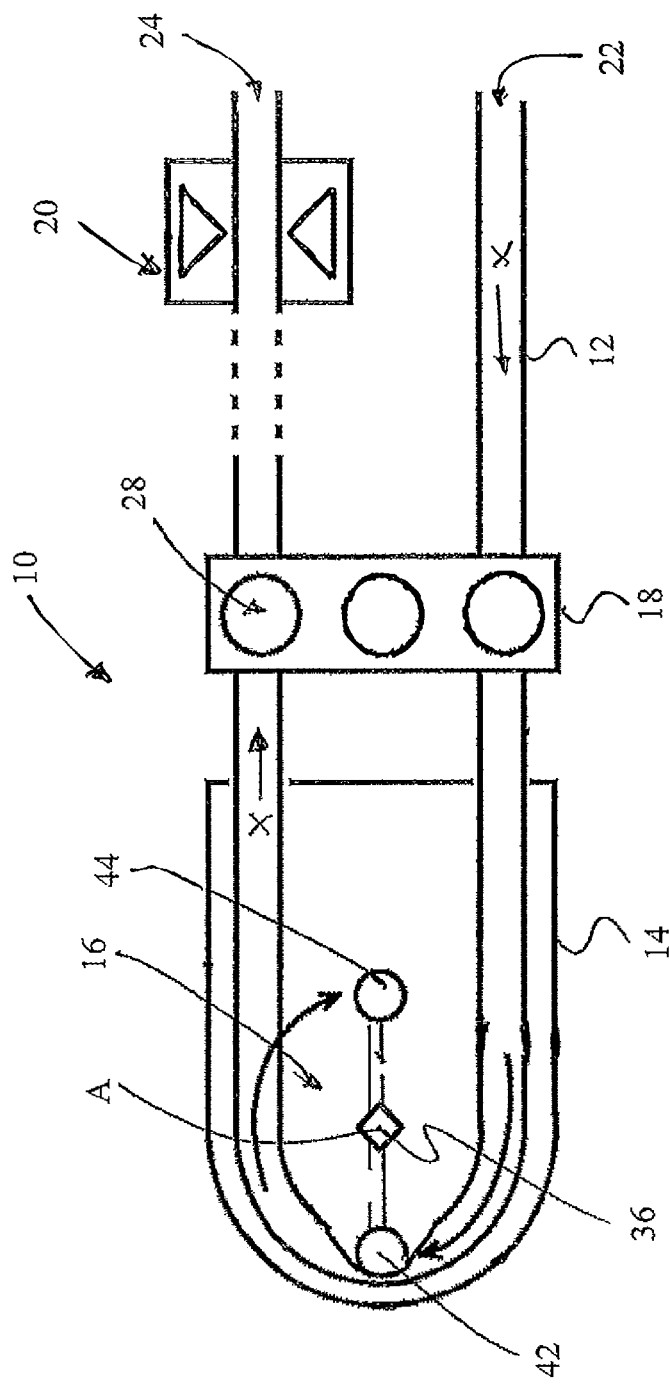
FIG. 4 is a schematic side view of the rotary peristaltic pump of FIG. 1 with the rollers in a third build up position.
Figure 5:
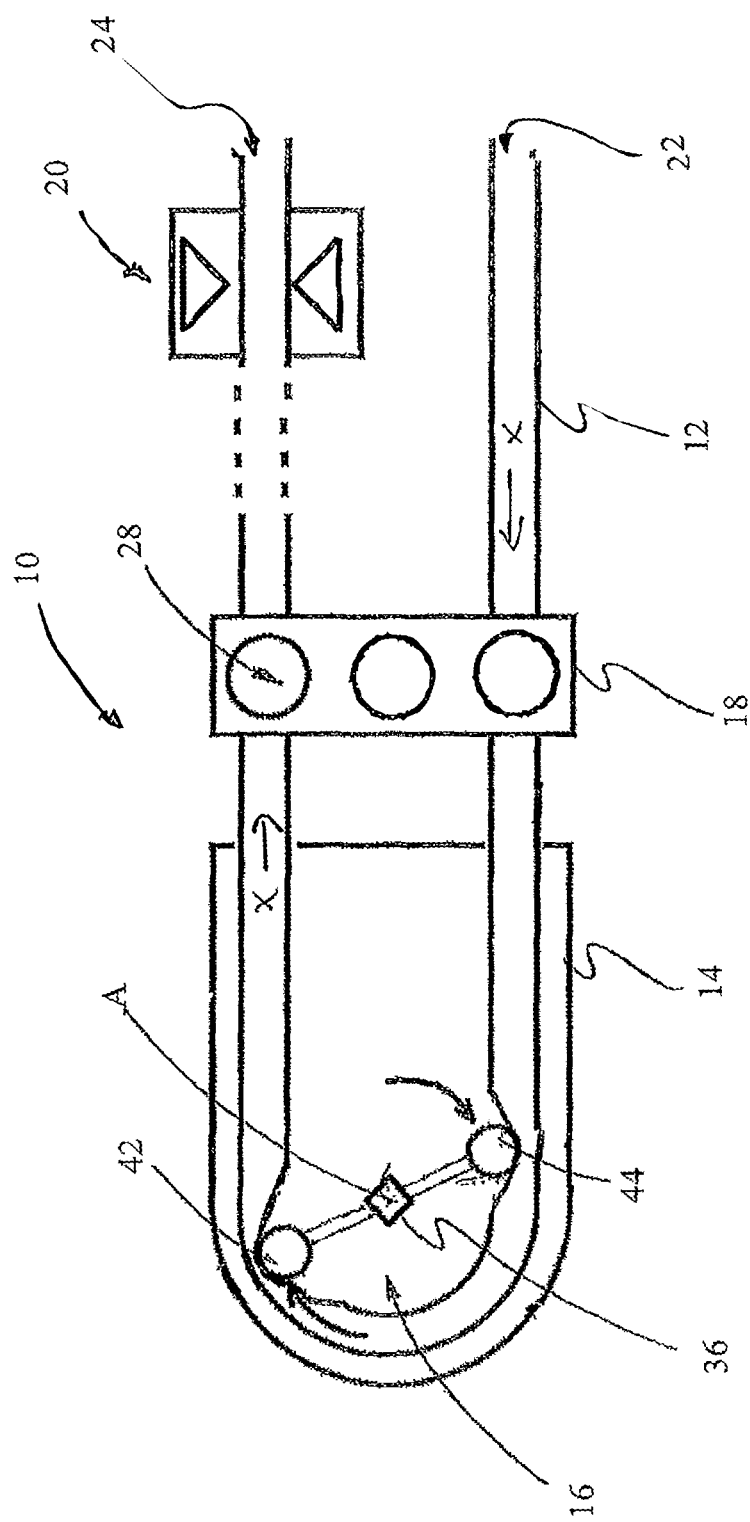
FIG. 5 is a schematic side view of the rotary peristaltic pump of FIG. 1 with the rollers in a position following a switchover rotation.
Figure 6:
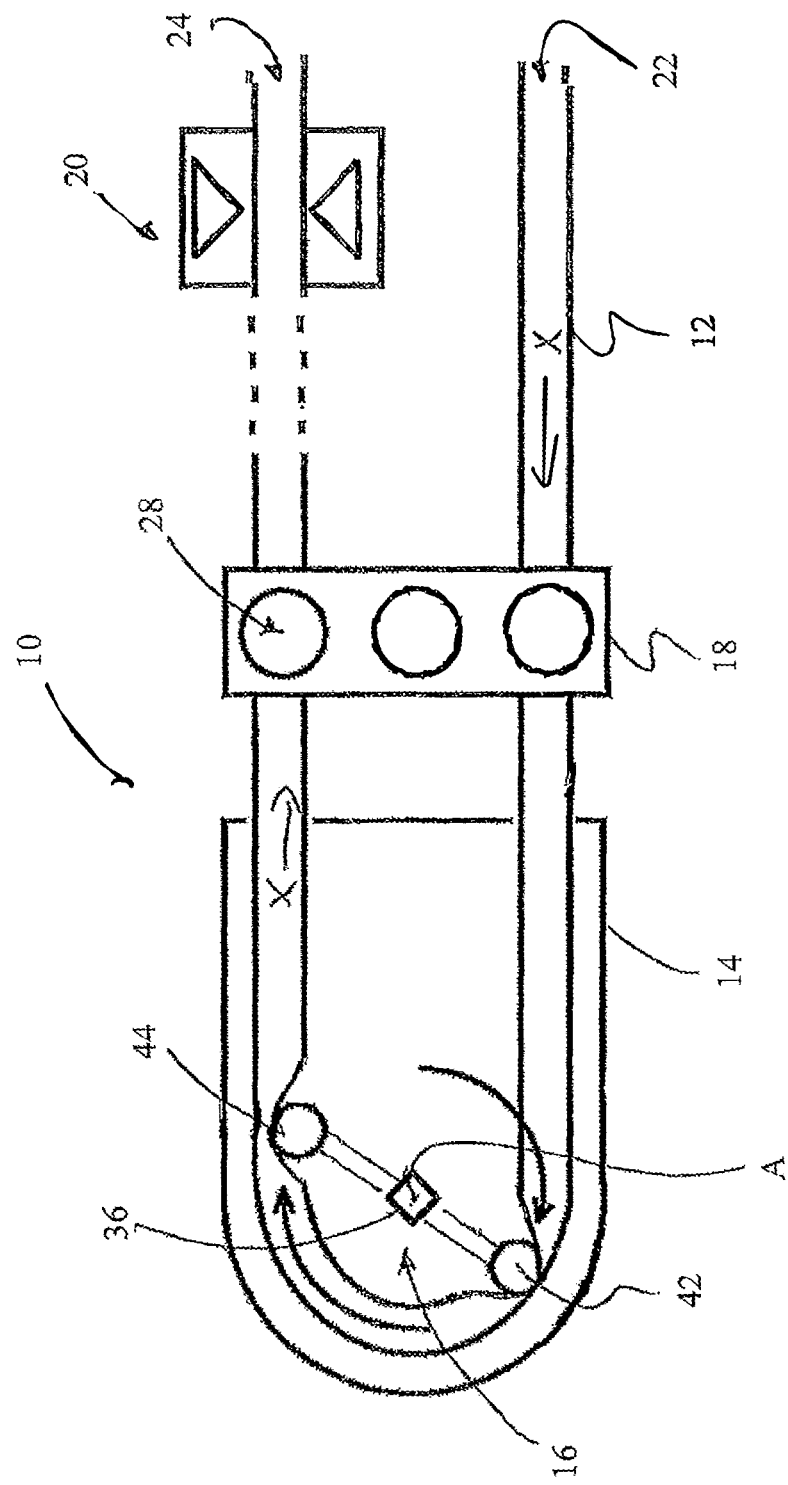
FIG. 6 is a schematic side view of the rotary peristaltic pump of FIG. 1 with the rollers in a fourth build up position.
Figure 7:
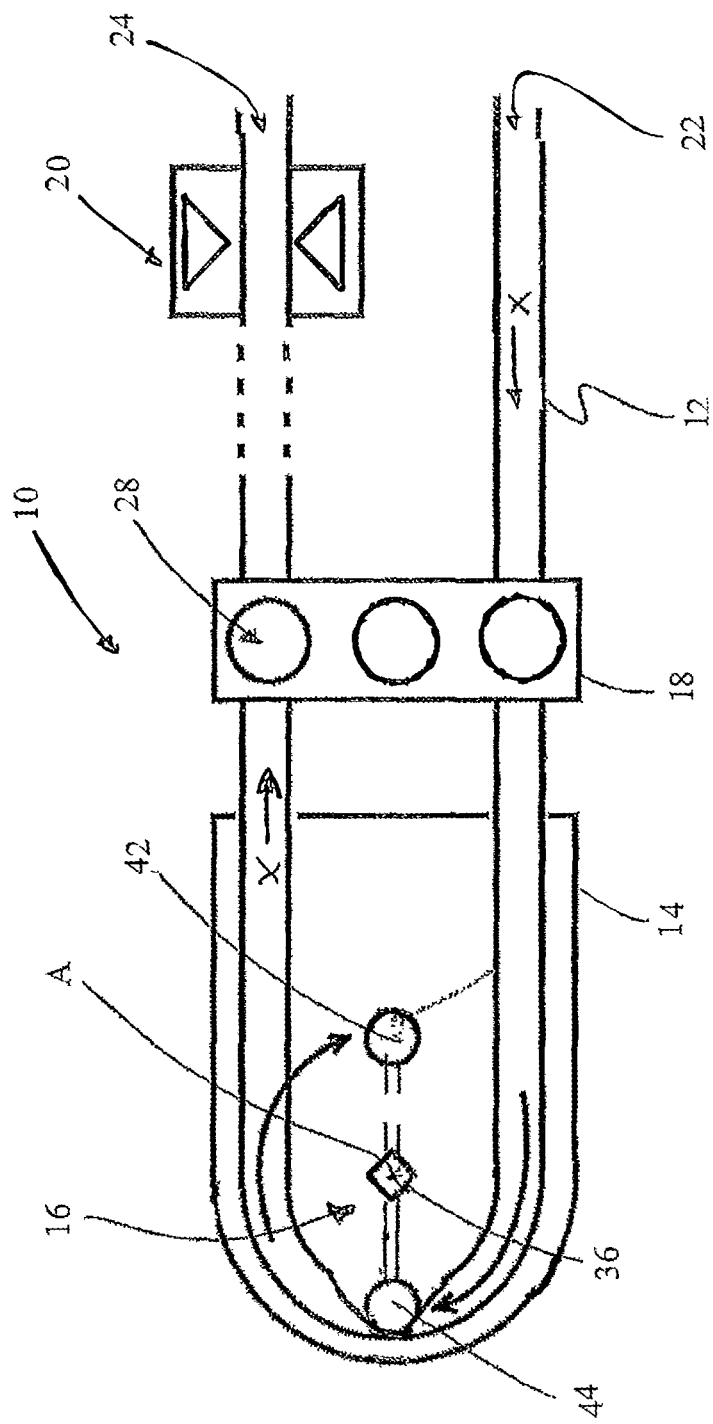
FIG. 7 is a schematic side view of the rotary peristaltic pump of FIG. 1 with the rollers in a fifth build up position.
Figure 8:
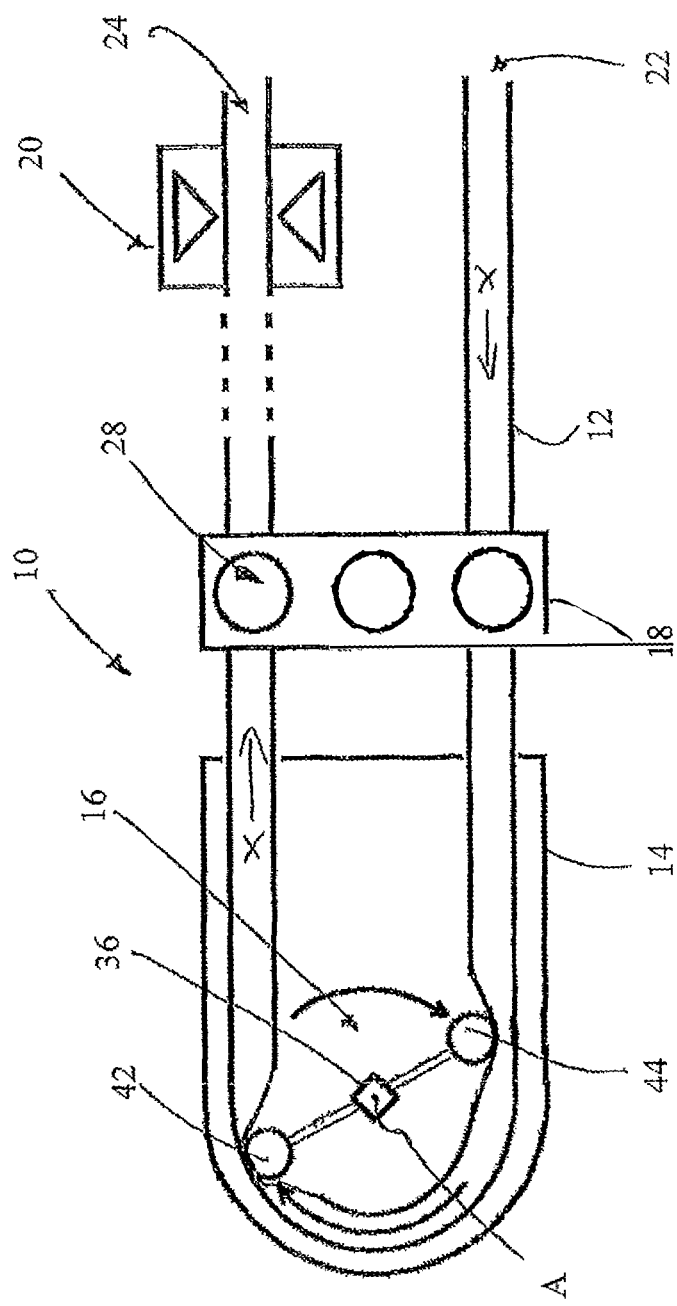
FIG. 8 is a schematic side view of the rotary peristaltic pump of FIG. 1 with the rollers in a sixth build up position.

Following the first repeat, the peristaltic pump rotor 16 will be in the position shown in FIG. 3 and following the second repeat the peristaltic pump rotor 16 will be in the position shown in FIG. 4, having been rotated through 240 degrees each time.

Following the operation of the rotary peristaltic pump 10 as described above, the peristaltic pump rotor 16 will be in the position shown in FIG. 4. At this point the roller 44 has been tested for correct occlusion of the tube 12 at two different angular displacements and the roller 42 has been tested for correct occlusion at one angular displacement.

The valve 20 is then closed and the peristaltic pump rotor 16 rotated by a predetermined switchover angle of 60 degrees (step k) of the claimed method). The test method described above is then repeated. This switchover rotation has the effect of switching the position of the peristaltic pump rotor 16 such that the roller 42 that has been tested at one angular displacement, can be tested at a further two angular displacements such that each of the rollers 42, 44 is tested at three different angular displacements, i.e. in three different angular positions relative to the drive axis A.

Generation of Alerts

At any point, if an alert signal 60 is generated by the CPU 54, the test cycle is ended and a fault displayed on an LCD screen (not shown) on the pump system 11.

If the roller 44 is defective or for some other reason cannot correctly occlude the flexible tube 12, there will be a pressure drop in the fluid downstream of the peristaltic pump rotor 16 and upstream of the valve 20 which will be measured by the pressure sensor 28 and/or a minimum operating pressure will not be reached.

In particular:—

If during the initial rotation of the peristaltic pump rotor 16, from the position shown in FIG. 1 to the position shown in FIG. 2, it can be concluded that the roller 44 is not sufficiently occluding the flexible tubing, if a pressure downstream of the peristaltic pump rotor 16 and upstream of the valve 20 does not reach a minimum threshold value. This minimum threshold value is the first predetermined threshold value. Specifically, the CPU 54 will generate an alert signal 60 if the pressure measured during the predetermined priming angular displacement does not reach a minimum level of 200 mmHg.

If during any rotation of the peristaltic pump rotor 16 immediately prior to a holding interval the pressure is not greater than the first predetermined threshold value, an alert signal will be generated.

If any measured pressure drop detected by the pressure sensor 28 is greater than a second predetermined threshold value, then it can be concluded that the roller 44 is not correctly occluding the tube 12 when the peristaltic pump rotor 16 is in this specific position during the holding interval for which the pressure drop is being measured. Specifically, if the calculated pressure drop during a particular holding interval, of e.g. 10 seconds, is in excess of 175 mmHg from the maximum recorded pressure, an alert signal will be generated.

The skilled person will recognise that the angular rotations of the rollers 42, 44 described above are the most efficient way of testing a two-arm rotary peristaltic pump 10, and the occlusion of two rollers 42, 44 in three different positions in the outer race. The skilled person will recognise that a more detailed test may be carried out by testing each roller 42, 44 in four or more positions in the outer race and will select an angular displacement suitable for such a test.

The skilled person will also recognise that this test method is applicable to rotary peristaltic pumps 10 with one or more than two rollers 42, 44 and/or one or more than two arms 38, 40, and that application of the method would require recalculation of the angular displacements for rotary peristaltic pumps 10 with more than two arms and/or rollers.

What is claimed is:

1. A method of testing the rotor engagement of a peristaltic pump, the method comprising the steps of:
   (a) providing a pump system comprising: a peristaltic pump rotor; a tube; a valve; a pressure sensor; a comparator; and a processor;
      wherein: the valve is situated on the tube downstream of the peristaltic pump rotor;
      the pressure sensor is arranged to sense the fluid pressure in the tube downstream of the peristaltic pump rotor and upstream of the valve;
      the peristaltic pump rotor includes at least one member having a tube contact portion; and
         the at least one member being rotatable about a drive axis to move the tube contact portion along an arcuate path, the tube contact portion being configured to occlude the tube;
   (b) closing the valve;
   (c) actuating the peristaltic pump rotor from a first rotor position to a second rotor position such that the peristaltic pump rotor is angularly displaced about the drive axis by a predetermined priming angular displacement;
   (d) holding the peristaltic pump rotor in the second rotor position for a holding interval;
   (e) measuring a maximum pressure of a fluid in the tube downstream of the peristaltic pump rotor during and/or after completing step c);
   (f) measuring any pressure drop of the fluid in the tube downstream of the peristaltic pump rotor during the holding interval;
   and
   (g) generating an alert signal if the maximum pressure recorded in step e) is below a first threshold value and/or the pressure drop measured in step f) is above a second threshold value.

2. The method according to claim 1, further comprising step h) which comprisese opening the valve and determining when the fluid pressure in the tube is lower than a third threshold.

3. The method according to claim 2, wherein steps b) to g) are repeated a primary predetermined number of times.

4. The method according to claim 3, wherein the primary predetermined number of times is two.

5. The method according to claim 2, further comprising step i), wherein step i) comprises actuating the peristaltic pump rotor such that the peristaltic pump rotor is angularly displaced about the drive axis by a predetermined switchover angle.

6. The method according to claim 5, wherein the predetermined switchover angle is in the range of 10 to 170 degrees.

7. The method according to claim 6, wherein the predetermined switchover angle is 60 degrees.

8. The method according to claim 5, wherein following the completion of step g), steps b) to g) are repeated a secondary predetermined number of times.

9. The method according to claim 8, wherein the secondary predetermined number of times is three.

10. The method according to claim 2, wherein the third threshold value is in the range of 0 mmHg (0 Pa) to 1450 mmHg (193317.47 Pa).

11. The method according to claim 2, wherein the third threshold value is 75 mmHg (9999.18 Pa).

12. The method according to claim 1, wherein:
the holding interval is in the range of 5 to 60 seconds;
the first threshold value is in the range of 75 mmHg (9999.18 Pa) to 1500 mmHg (199983.59 Pa);
the second threshold value is in the range of 50 mmHgs to 1475 mmHgs or 0.83 mmHgs$^{-1}$ (111.10 Pas$^{-1}$) to 295 mmHgs$^{-1}$ (39330.11 Pas$^{-1}$);
the priming angular displacement is in the range of 10 to 350 degrees;
the processor is used to generate a pass signal if no alert signals are generated; and
the alert signal is used to generate an alarm signal.

13. The method according to claim 12, wherein the alarm signal is generated by a signal generator.

14. The method according to claim 13, wherein the alarm signal is audio and/or visual.

15. The method according to claim 1, wherein the method is terminated when an alert signal is generated.

16. The method according to claim 1, wherein:
the fluid being pumped is blood, or
the fluid being pumped is saline solution and/or blood dialysis fluid; and
the tube is held within a U-Shaped channel in an outer race of a housing;
the pump system automatically runs the method when the pump system is activated;
the valve is a pinch clamp configured to occlude the tube; and
the tube contact portion comprises a roller.

17. The method according to claim 1, wherein the at least one member comprises two members.

18. The method according to claim 17, wherein the two members are diametrically opposed.

19. The method according to claim 1, wherein the at least one member comprises three members.

20. The method according to claim 19, wherein the three members are equally spaced angularly about the drive axis.

* * * * *

UNITED STATES PATENT AND TRADEMARK OFFICE
CERTIFICATE OF CORRECTION

PATENT NO. : 11,365,728 B2
APPLICATION NO. : 16/488499
DATED : June 21, 2022
INVENTOR(S) : Eric Westenbrink It is certified that error appears in the above-identified patent and that said Letters Patent is hereby corrected as shown below:

In the Claims

At Claim 10, Column 9, Lines 1-3, please replace "10. The method according to claim 2, wherein the third threshold value is in the range of 0 mmHg (0 Pa) to 1450 mmHg (193317.47 Pa)." with --10. The method according to claim 1, wherein: the holding interval is in the range of 5 to 60 seconds; the first threshold value is in the range of 75 mmHg (9999.18Pa) to 1500mmHg (199983.59Pa); the second threshold value is in the range of 50 mmHg (6666.12Pa) to 1475 mmHg (196650.53 Pa) or 0.83 mmHgs$^{-1}$(111.10Pas$^{-1}$) to 295 mmHgs$^{-1}$(39330.11Pas$^{-1}$); the priming angular displacement is in the range of 10 to 350 degrees; the processor is used to generate a pass signal if no alert signals are generated; and the alert signal is used to generate an alarm signal.--

At Claim 11, Column 9, Lines 4-5, please replace "11. The method according to claim 2, wherein the third threshold value is 75mmHg (9999.18 Pa)." with --11. The method according to claim 2, wherein the third threshold value is in the range of 0 mmHg (0Pa) to 1450 mmHg (193317.47Pa).--

At Claim 12, Column 9, Lines 6-18, please replace "12. The method according to claim 1, wherein the holding interval is in the range of 5 to 60 seconds; the first threshold value is in the range of 75 mmHg (9999.18 Pa) to 1500 mmHg (199983.59 Pa); the second threshold value is in the range of 50 mmHgs to 1475 mmHgs or 0.83 mmHgs$^{-1}$ (111.10 Pas$^{-1}$) to 295 mmHgs-1 (39330.11 Pas$^{-1}$); the priming angular displacement is in the range of 10 to 350 degrees; the processor is used to generate a pass signal if no alert signals are generated; and the alert signal is used to generate an alarm signal." with --12. The method according to claim 2, wherein the third threshold value is 75 mmHg (9999.18Pa).--

At Claim 13, Column 9, Lines 19-20, please replace "13. The method according to claim 12, wherein the alarm signal is generated by a signal generator." with --13. The method according to claim 10, wherein the alarm signal is generated by a signal generator.--

Signed and Sealed this
Fifteenth Day of August, 2023

Katherine Kelly Vidal
*Director of the United States Patent and Trademark Office*